(12) United States Patent
Deischinger et al.

(10) Patent No.: US 11,382,595 B2
(45) Date of Patent: Jul. 12, 2022

(54) METHODS AND SYSTEMS FOR AUTOMATED HEART RATE MEASUREMENT FOR ULTRASOUND MOTION MODES

(71) Applicant: GE Precision Healthcare LLC, Milwaukee, WI (US)

(72) Inventors: Harald Deischinger, Schlatt (AT); Walter Duda, Jr., Regau (AT)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 60 days.

(21) Appl. No.: 17/005,621

(22) Filed: Aug. 28, 2020

(65) Prior Publication Data

US 2022/0061798 A1 Mar. 3, 2022

(51) Int. Cl.
*A61B 8/02* (2006.01)
*A61B 8/08* (2006.01)
*A61B 8/00* (2006.01)
*A61B 90/00* (2016.01)

(52) U.S. Cl.
CPC ............... *A61B 8/02* (2013.01); *A61B 8/461* (2013.01); *A61B 8/5215* (2013.01); *A61B 90/06* (2016.02)

(58) Field of Classification Search
CPC ...................................................... A61B 8/02
See application file for complete search history.

(56) References Cited

U.S. PATENT DOCUMENTS

| 9,366,754 | B2 | 6/2016 | Buckton et al. |
| 9,392,995 | B2 | 7/2016 | Perrey et al. |
| 10,675,005 | B2 | 6/2020 | Viggen |
| 2017/0119343 | A1* | 5/2017 | Pintoffl ................ A61B 8/02 |
| 2017/0258437 | A1* | 9/2017 | Maeda ............... A61B 8/4483 |
| 2020/0226757 | A1* | 7/2020 | Hare, II .................. G06N 3/08 |
| 2021/0267570 | A1* | 9/2021 | Ulman ............... A61B 8/5246 |

* cited by examiner

*Primary Examiner* — Serkan Akar
*Assistant Examiner* — Aminah Asghar
(74) *Attorney, Agent, or Firm* — McAndrews, Heid & Malloy, Ltd.; Jacob Groethe; David Bates

(57) ABSTRACT

Systems and methods are provided for automated heart rate measurement for ultrasound motion modes. Dataset may be acquired, based on a particular medical imaging technique, during medical examination of an area that includes heart tissue, medical images may be generated based on the acquired dataset, and the medical images may be displayed. At least one of the medical images or imaging data corresponding to the at least one of the medical images may be processed, in real-time, position of at least one of a plurality of calipers used in measuring heartrate may be automatically determined based on processing of the at least one of the medical images or the imaging data, and the plurality of calipers may be automatically indicated in the medical images, based on the position of the at least one of the plurality of calipers, during the displaying of the medical image.

10 Claims, 10 Drawing Sheets

METHODS AND SYSTEMS FOR AUTOMATED HEART RATE MEASUREMENT FOR ULTRASOUND MOTION MODES

FIELD

Aspects of the present disclosure relate to medical imaging. More specifically, certain embodiments relate to methods and systems for automated heart rate measurement for ultrasound motion modes.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Medical imaging systems may be used to conduct particular types of examination. For example, in some instances, medical imaging systems may be used in examining the heart and functions thereof. Use of medical imaging systems in conjunction with such examination, however, poses certain challenges, particularly with respect to assessing outcome of the examination.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for automated heart rate measurement for ultrasound motion modes, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
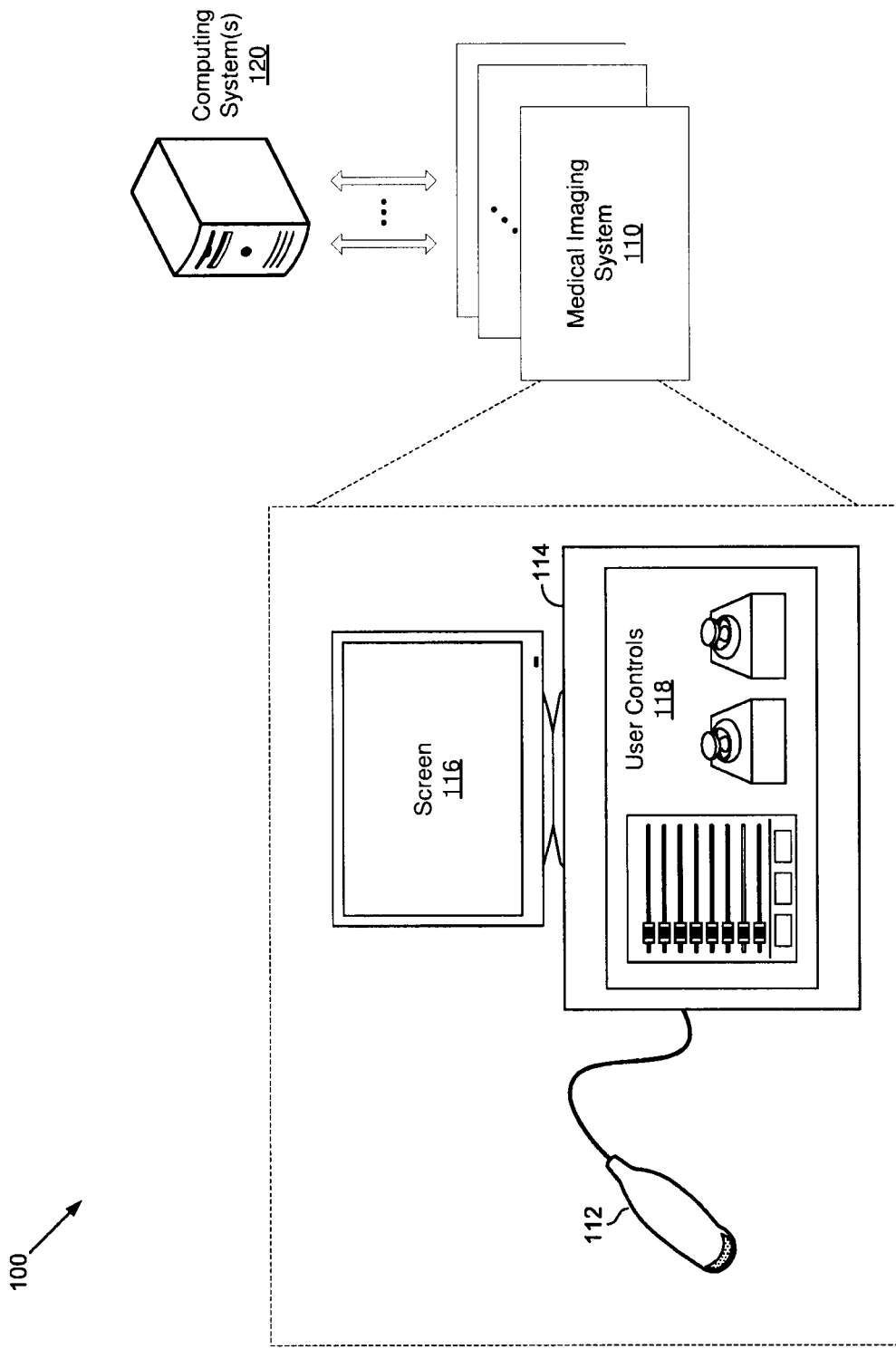
FIG. 1 is a block diagram illustrating an example medical imaging arrangement that may be configured for supporting automated heart rate measurement for ultrasound motion modes.

Certain implementations in accordance with the present disclosure may be directed to automated heart rate measurement for ultrasound motion modes. In particular, various embodiments have the technical effect of enhancing quality of heart examination using medical imaging, by allowing for automatic and real-time determination and display of calipers or markers that may be used in measuring heartrate, particularly fetal heartrate (FHR) measurements. This may be done, for example, by processing medical images or data corresponding thereto, such as using sliding window, to identify best position for at least one of the calipers. The position of remaining caliper(s) may be determined in the same manner or based on the already determined position(s) of the caliper(s), such as based on measured heartrate. In some instances, artificial intelligence (AI) based techniques may be used to facilitate or support the automatic identifying and/or calculation of caliper positions. Aspects of the present disclosure have the technical effect of allowing for heart examinations that are more reliable and with enhanced workflow.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, processing to form images, including beamforming, is performed in software, firmware, hardware, or a combination thereof. One example implementation of an ultrasound system having a software beamformer architecture formed in accordance with various embodiments as illustrated in FIGS. 1 and 2 (or just FIG. 2).

Figure 2:
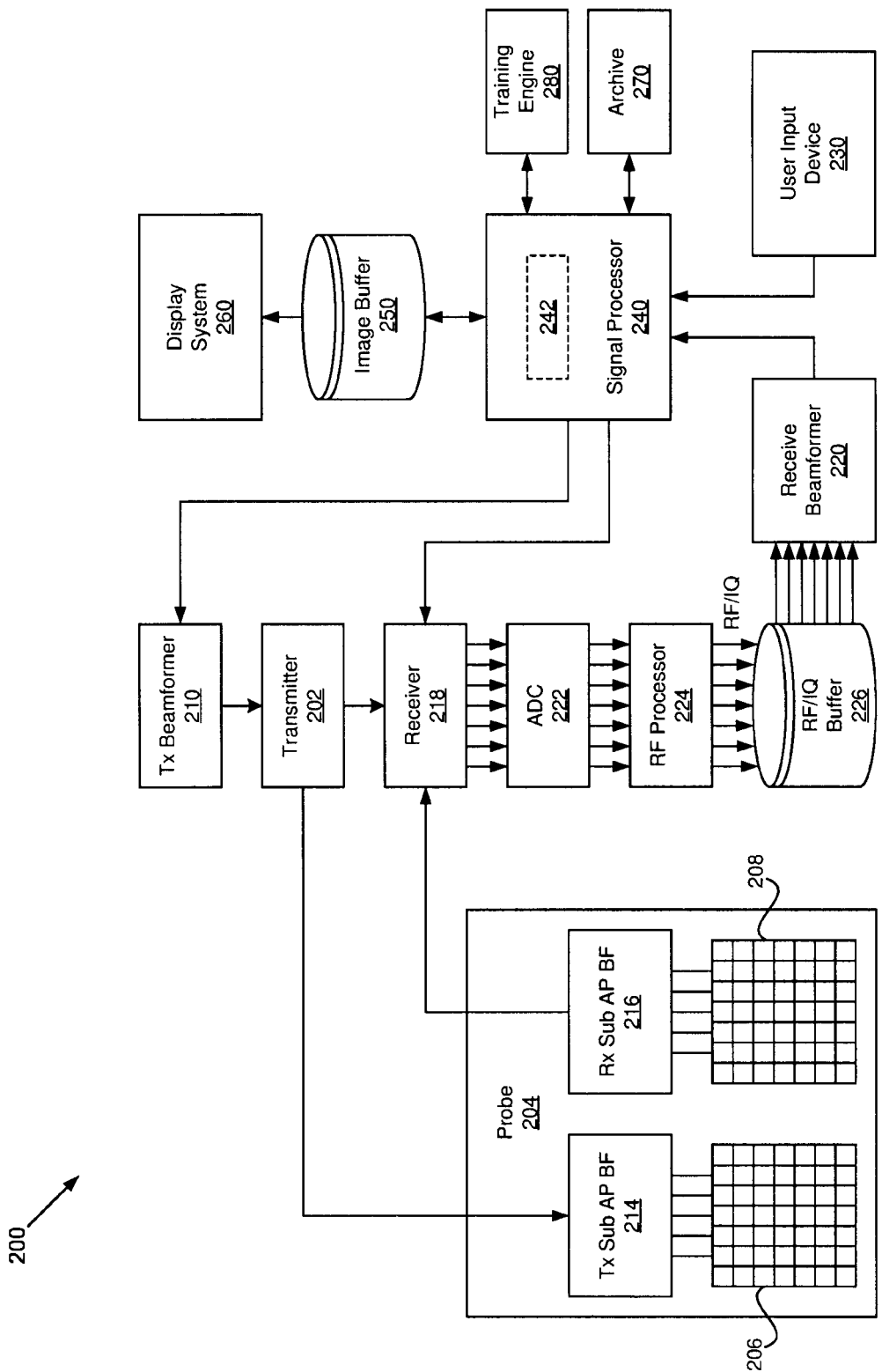
FIG. 2 is a block diagram illustrating an example ultrasound system that may be configured for supporting automated heart rate measurement for ultrasound motion modes.

FIG. 1 is a block diagram illustrating an example medical imaging arrangement that may be configured for supporting automated heart rate measurement for ultrasound motion modes. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system, which may correspond to the medical imaging system 110, is described in more detail with respect to FIG. 2. As shown in FIG. 1, the medical imaging system 110 may comprise a scanner device 112, which may be portable and movable, and a display/control unit 114.

The scanner device 112 may be configured for generating and/or capturing particular type of imaging signals (and/or data corresponding thereto), such as by being moved over a patient's body (or part thereof), and may comprise suitable circuitry for performing and/or supporting such functions.

The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost—e.g., by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110.

In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In various implementations, medical imaging systems (e.g., the medical imaging system 110) may be configured to support automated heart rate measurement for ultrasound motion modes. This is described in more detail below.

FIG. 2 is a block diagram illustrating an example ultrasound system that may be configured for supporting automated heart rate measurement for ultrasound motion modes. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1.

The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270.

For example, the user input device 230 may include button(s), rotary encoder(s), a touchscreen, motion tracking, voice recognition, a mouse device, keyboard, camera and/or any other device capable of receiving user directive(s). In certain embodiments, one or more of the user input devices 230 may be integrated into other components, such as the display system 260 or the ultrasound probe 204, for example.

As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise an automated heartrate measurement module 242, which comprises suitable circuitry, interfaces, logic, and/or code that may be configured to perform and/or support various functions or operations relating to, or in support of automated heart rate measurement for ultrasound motion modes, as described in more detail below.

In some implementations, the signal processor 240 (and/or components thereof, such as the automated heartrate measurement module 242) may be configured to implement and/or use artificial intelligence and/or machine learning techniques to enhance and/or optimize imaging related functions or operations. For example, the signal processor 240 (and/or components thereof, such as the automated heartrate measurement module 242) may be configured to implement and/or use deep learning techniques and/or algorithms, such as by use of deep neural networks (e.g., a convolutional neural network (CNN)), and/or may utilize any suitable form of artificial intelligence image analysis techniques or machine learning processing functionality, which may be configured to analyze acquired ultrasound images, such as to identify, segment, label, and track structures (or tissues thereof) meeting particular criteria and/or having particular characteristics.

In an example implementation, the signal processor 240 (and/or components thereof, such as the automated heartrate measurement module 242) may be provided as a deep neural network, which may be made up of, for example, an input layer, an output layer, and one or more hidden layers in between the input and output layers. Each of the layers may be made up of a plurality of processing nodes that may be referred to as neurons. For example, the deep neural network may include an input layer having a neuron for each pixel or a group of pixels from a scan plane of an anatomical structure, and the output layer may have a neuron corresponding to a plurality of pre-defined structures or types of structures (or tissue(s) therein). Each neuron of each layer may perform a processing function and pass the processed ultrasound image information to one of a plurality of neurons of a downstream layer for further processing.

As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The neurons of a fourth layer may learn characteristics of particular tissue types present in particular structures, etc. Thus, the processing performed by the deep neural network (e.g., convolutional neural network (CNN)) may allow for identifying biological and/or artificial structures in ultrasound image data with a high degree of probability.

In some implementations, the signal processor 240 (and/or components thereof, such as the automated heartrate measurement module 242) may be configured to perform or otherwise control at least some of the functions performed thereby based on a user instruction via the user input device 230. As an example, a user may provide a voice command, probe gesture, button depression, or the like to issue a particular instruction, such as to initiate and/or control various aspects of heart imaging related operations, such as automated heartrate measurements, including artificial intelligence (AI) based analysis of heart functions and/or real-time and automated measurements and/or analysis, and/or to provide or otherwise specify various parameters or settings relating thereto, as described in more detail below.

The training engine 280 may comprise suitable circuitry, interfaces, logic, and/or code that may be operable to train the neurons of the deep neural network(s) of the signal processor 240 (and/or components thereof, such as the automated heartrate measurement module 242). For example, the signal processor 240 may be trained to identify particular structures and/or tissues (or types thereof) provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the automated heartrate measurement module 242) with respect to the characteristics of the particular structure(s), such as the appearance of structure edges, the appearance of structure shapes based on the edges, the positions of the shapes relative to landmarks in the ultrasound image data, and the like, and/or with respect to characteristics of particular tissues (e.g., softness thereof). In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support automated heart rate measurement for ultrasound motion mode. This is described in more detail below.

Figure 3:
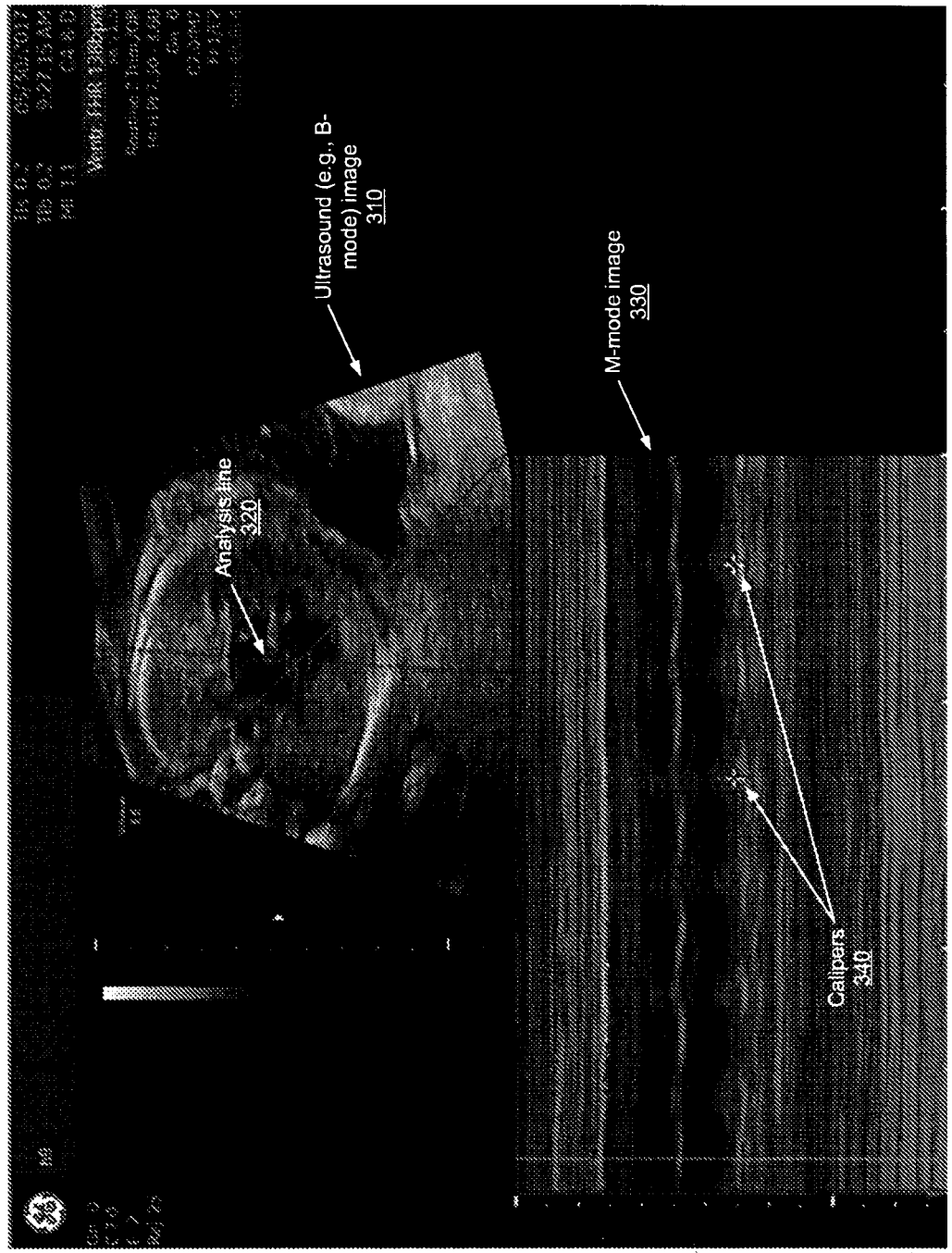
FIG. 3 illustrates an example use scenario when using a medical imaging system to measure heartrate.

FIG. 3 illustrates an example use scenario when using a medical imaging system to measure heartrate. Shown in FIG. 3 is a screenshot 300 of image(s) generated in an example medical imaging system during heart function examination.

In this regard, medical imaging systems (e.g., medical imaging system 110 of FIG. 1, the ultrasound system 200 of FIG. 2) may be configured for supporting particular types of examinations and/or operations associated therewith. For example, medical imaging systems may be configured for performing heart related examinations, and further in facilitating obtaining measurements associated therewith, such as heartrate measurements. Such examinations may be particularly useful when examining fetus' heart and/or obtaining measurement relating thereto—e.g., fetal heartrate (FHR) measurement. In this regard, heartrate measurements may be obtained based on tracking of movement of the heart, such as by identifying a particular structure in the heart, and then tracking movement of that structure, with the heartrate being calculated or otherwise determined based on that tracking of movement.

In some instance, measuring heart rate may be performed by, for example, placing calipers (also referred as markers) on time-scale images obtained or generated during medical images, with this markers being calipers being set to enable tracking repeated movement of the heart (or, specifically, a particular structure of the heart). This is shown in the example use scenario illustrated in FIG. 3. In this regard, shown in the screenshot 300 is an ultrasound (e.g., B-Mode) image 310 obtained during ultrasound imaging/examination (e.g., of a fetus). A corresponding time motion M-mode image 330 (e.g., "anatomical M-Mode" image as shown in FIG. 3, sometimes also referred to as "virtual M-Mode" image) is generated, such as based on a particular line 320 (referred to hereafter as "analysis line") through the heart. In this regard, the M-mode image 330 shows temporal changes in ultrasound waves along the chosen ultrasound line. Thus, the M-mode image 330 represents time-scale (that is time-based) of a cross-sectional area in a body part or structure captured in the B-Mode, and therefore show time-scale based changes or movement in that area. In other words, the x-axis in the M-mode image 330 represent the time axis, thus allowing for tracking of changes area corresponding to the analysis line 320 through time.

The system user (e.g., ultrasound technician) may manually select and/or adjust the analysis line 310. Thus, the system user may optimize the quality of the M-mode image 330, such as by carefully selecting the analysis line 320 to run through or bisect a particular structure (e.g., one of the ventricles of the heart), to enable tracking motion of that structure, which allows tracking motion of the heart (vs. time). Once the analysis line 320 is selected, and the corresponding M-mode image 330 is generate, calipers (also referred as markers) may be placed within the time-based image, particularly at the same point in repeated wave, to track motion of the heart. For example, in the example use scenario shown in FIG. 3, two calipers 340 (green and yellow cross) are placed in the M-mode image 330, to measure the time-length of a number of heart cycles (e.g., 2 heart cycles, as shown in FIG. 3), which enables calculating the heartrate. In this regard, measuring the time between the calipers 340, based on the time-scale of the M-mode image 330 allows for measurement of the heartrate, which may then be displayed (e.g., shown as "Ventr. FHR 138 bpm" in the screenshot 300).

In conventional solutions, most of the steps related to the measurements (e.g., of heartrates, as described above) are done manually by the system user. Performing measurement in such manual manner may have some disadvantages, however, as it may pose some challenges and/or may have some drawbacks. For example, placing calipers (e.g., with such input devices as trackball) may be a tedious task. Further, selecting the optimal analysis line may be difficult, especially for less-experienced users.

Implementations in accordance with the present disclosure may address some of the disadvantages of conventional solutions, particularly by automating various aspects of heartrate measurements. For example, automatic determination and/or suggestion of caliper positions may be automated, to optimize and reduce time need for placement of the calipers, which may save time for workflow, thus speeding workflow. In this regard, in some instances automatic placing calipers may be further enhanced to ensure selecting and/or suggesting more "natural position," to increases the likelihood of users' acceptance of the feature. Also, in some instances, manual checkup and corrections may be allowed. Automated placement of calipers for measurement of (fetal) heart rate may be particularly suitable in motion and Doppler modes (e.g. M-Mode, MC-Mode, anatomical M-Mode, PW-Mode, CW-Mode) based ultrasound imaging. In some implementations, selection and placement of analysis lines used in obtaining timing based images (or data/charts based thereon) may also be automated.

Thus, with reference to the screenshot 300 shown in FIG. 3, in implementations in accordance with the present disclosure, the placement of the markers/calipers 340 (and in some instances the selection of the analysis line 320) may be performed automatically in the imaging systems. For example, in the ultrasound system 200 of FIG. 2, for example, this may be done via the processor 240 (and, particularly, using the automated heartrate measurement module 242). This may be done, for example, using pre-installed software (e.g., pre-defined data, pre-programmed algorithms, artificial intelligence functions, etc.) configured for optimal selection and placement of these elements. For example, the automated heartrate measurement module 242 may be configured to support automated measurement of the heartrate, by automatically placing 2 markers/calipers on time-series obtained from captured images, with the markers being used to measure a time difference between two or more cycles, thus allowing for measurement of heart rate. In some instances, artificial intelligence (AI) may be used. Deep neural networks may be used (and are continually updated for), for example, optimal placement of the markers/calipers (and, in some instances, selection of analysis lines).

Figure 4:
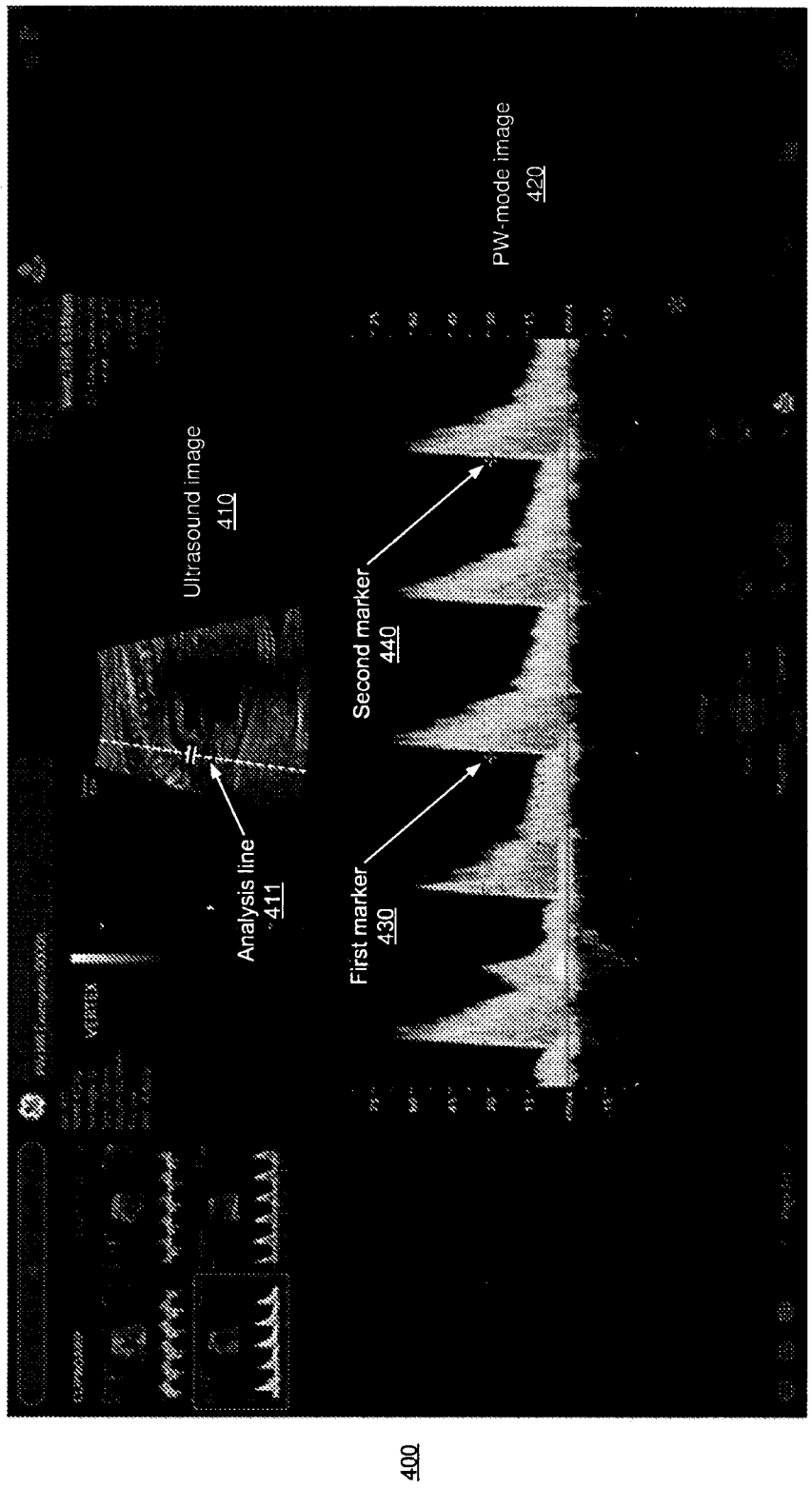
FIG. 4 illustrates an example use scenario in a medical imaging system performing automated heartrate measurement.

FIG. 4 illustrates an example use scenario in a medical imaging system performing automated heartrate measurement. Shown in FIG. 4 is a screenshot 400 of image(s) generated in an example medical imaging system (e.g., the medical imaging system 110 of FIG. 1, the ultrasound system 200 of FIG. 2) configured for supporting automated heartrate measurement.

In this regard, the screenshot 400 illustrates an ultrasound (e.g., B-Mode) image 410 obtained during ultrasound imaging/examination (e.g., of a fetus), with a corresponding PW-mode image 420, generated in the manner described above with respect to FIG. 3. However, the PW-mode image 420 (or data corresponding thereto) may be used, and (optionally) may be adjusted based on analysis or processing for automated heartrate measurement. In this regard, before initiating the automated heartrate measurement, the system user (e.g., ultrasound technician) may still need to focus on or identify the relevant structure before the automatic measurement (e.g., by selecting/setting an analysis line 411, and focus point therein (represent as the two horizontal lines in the analysis line).

The system may then perform the heartrate measurement, and may generate and display two corresponding caliper/markers 430 and 440, corresponding to and based on the measured heartrate. In some implementations, the automated heartrate measurements and related determination (e.g., the positions of the calipers/markers) may be based on use of sliding windows. An example of such implementation is described in more detail with respect to FIG. 5.

Figure 5:
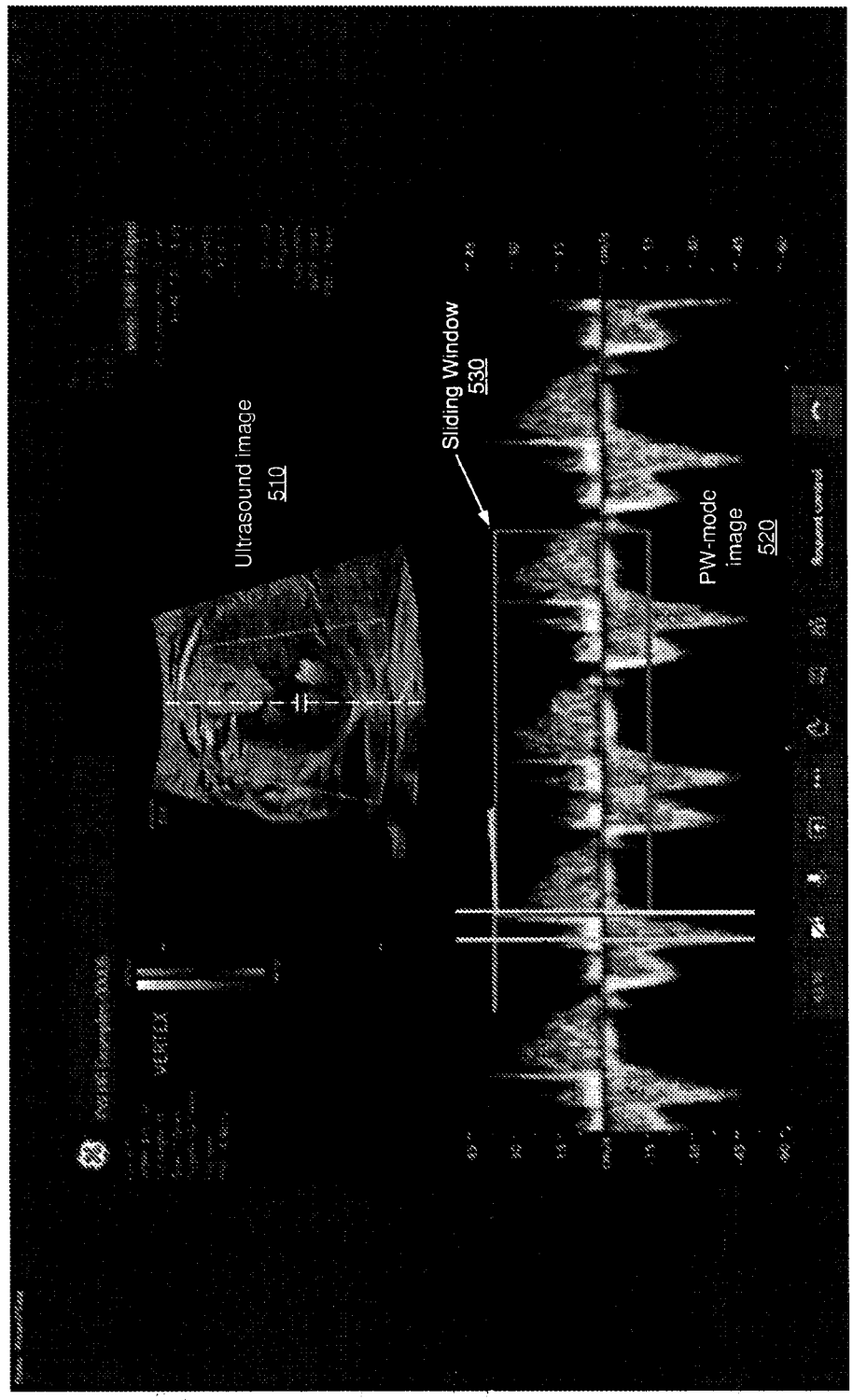
FIG. 5 illustrates use of sliding window based automated heart rate measurement in an example medical imaging system.

FIG. 5 illustrates use of sliding window based automated heart rate measurement in an example medical imaging system. Shown in FIG. 5 is a screenshot 500 illustrating implementation of sliding window based automated heart rate measurement in a medical imaging (e.g., the medical imaging system 110 of FIG. 1, the ultrasound system 200 of FIG. 2).

The screenshot 500 illustrates an ultrasound (e.g., B-Mode) image 510 obtained during ultrasound imaging/examination (e.g., of a fetus), with a corresponding PW-mode image 520, generated in the manner described above with respect to FIG. 3. In accordance with an example implementation, the PW-mode image 520 (and data corresponding thereto) may be used to perform sliding window based automated heart rate measurement.

In this regard, when implementing a sliding window based automated heart rate measurement, the system may calculate the heartrate (HR) and quality measures based on a sliding window 530, as shown in FIG. 5. It should be noted, however, that the sliding window is not actually display as screenshot 500 may suggest; rather, the sliding window 530 as shown in that screenshot is merely for illustrative purposes, and in actual use scenario the system create such "window" after the user initiates the automatic measurement when analyzing the dataset corresponding to the image but does not actually display that window. Certain window parameters may be set—e.g., window width be set to particular duration (e.g., 1 second), with the window being partition into a plurality of positions (e.g., every 0.1 sec). In some instances, portions of the analyzed image may be removed or ignored—e.g., top and bottom of the ultrasound data is cut off, as it does not contain useful data (rather, only noise and/or maternal movement). The HR and window position with the highest quality score may be taken. In this regard, the start of the window and calculated HR may be a first estimate to place the calipers.

In some instances, the position of the calipers (markers) may be adjusted. This may be done for various reasons. For example, even where the HR measurement may be correct, the position of the calipers may not be very "pleasing" and as such the position may need to be optimized. Samples within a range round the determined start position (e.g., +/−half of a heartrate) may be assessed to determine an adjusted position, such as based on higher brightness, which may be determining based on sum calculated over all samples along each ultrasound data line (e.g., PW/M). The position with the maximum sum may then be taken as new position—that is, the start position, which would be the position first (left) caliper, may be moved to the brightest line. The position of the second (right) caliper is then calculated, such as using the heartrate, and set at relative based to the first position, such based on a number of cycles (e.g., 2 cycles), which may be configured in the measure setup. These steps are illustrated and described in more detail with respect to FIGS. 6A-6E, below.

FIGS. 6A-6E illustrate an example workflow during use of sliding window based automatic heart measurement. Shown in FIGS. 6A-6E is a sequence of screenshots of images (and charts based on corresponding datasets) generated in an example medical imaging system configured for supporting automatic heart measurement (e.g., medical imaging system 110 of FIG. 1, the ultrasound system 200 of FIG. 2), particularly using sliding window based solutions.

Figure 6A:
FIGS. 6A-6E illustrate an example workflow during use of sliding window based automatic heart measurement.

FIG. 6A illustrates a screenshot 600. In this regard, the screenshot 600 corresponds to displayed image(s) in a medical imaging system during a medical (e.g., ultrasound) imaging examination, after the acquisition of the ultrasound images but before any measurement therein—e.g., when the user may starts automated heartrate measurement. The screenshot 600 includes a B-mode image 602 of fetus heart in the top, and a time-based PW-mode image 604 in the bottom, corresponding to a particular line in the B-mode image 602. The x-axis in the PW-mode image 604 is represent the time axis.

Figure 6B:
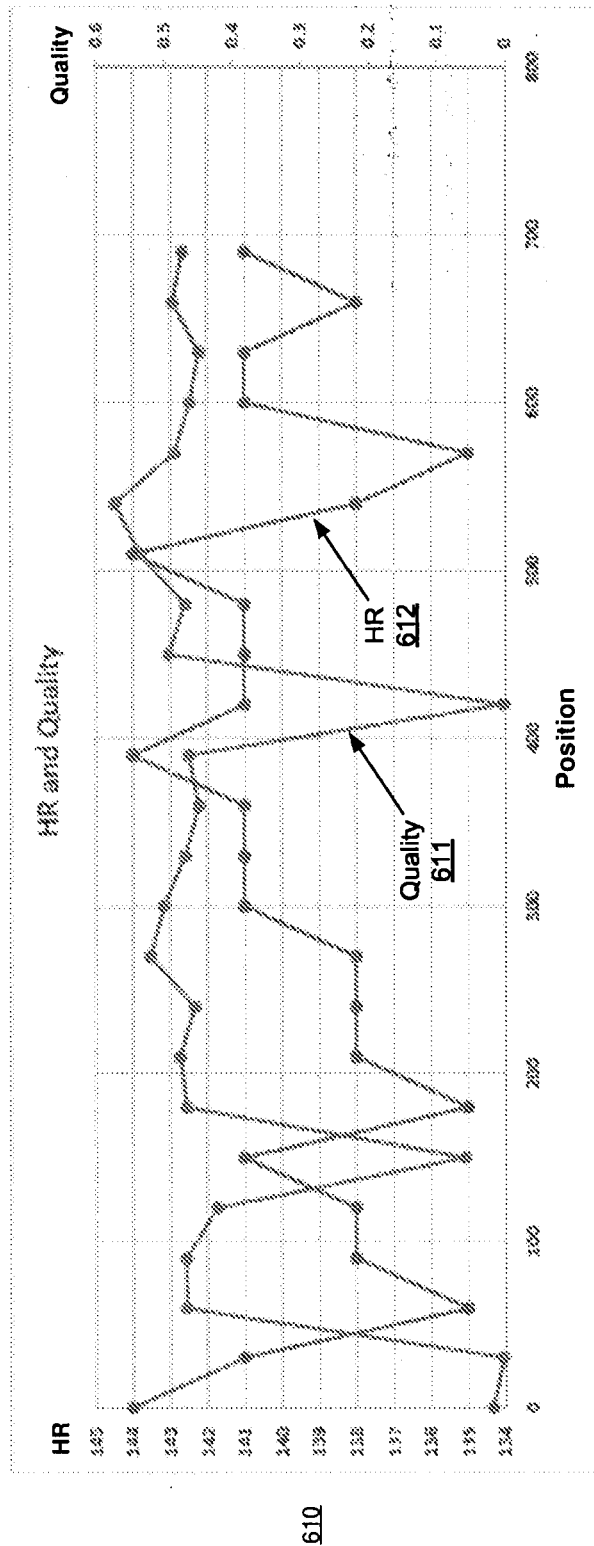

FIG. 6B illustrates a graph 610 with heartrate (HR) and quality scores for each position of an example sliding window applied to, and used for analysis of the PW-mode image 604 in FIG. 6A during automated heart rate measurement. In this regard, the HR and quality scores may be determined based analysis of the dataset corresponding to the PW-mode image 602 (particularly within a particular time sequence). The HR and quality scores may be used in determining a starting position. In the example use case shown in FIG. 6B, the graph 610 may correspond to full time sequence of around 3.5 seconds, with steps of 0.1 sec. this may yield 24 (possible) starting positions for a window with width of 1 second.

Figure 6C:
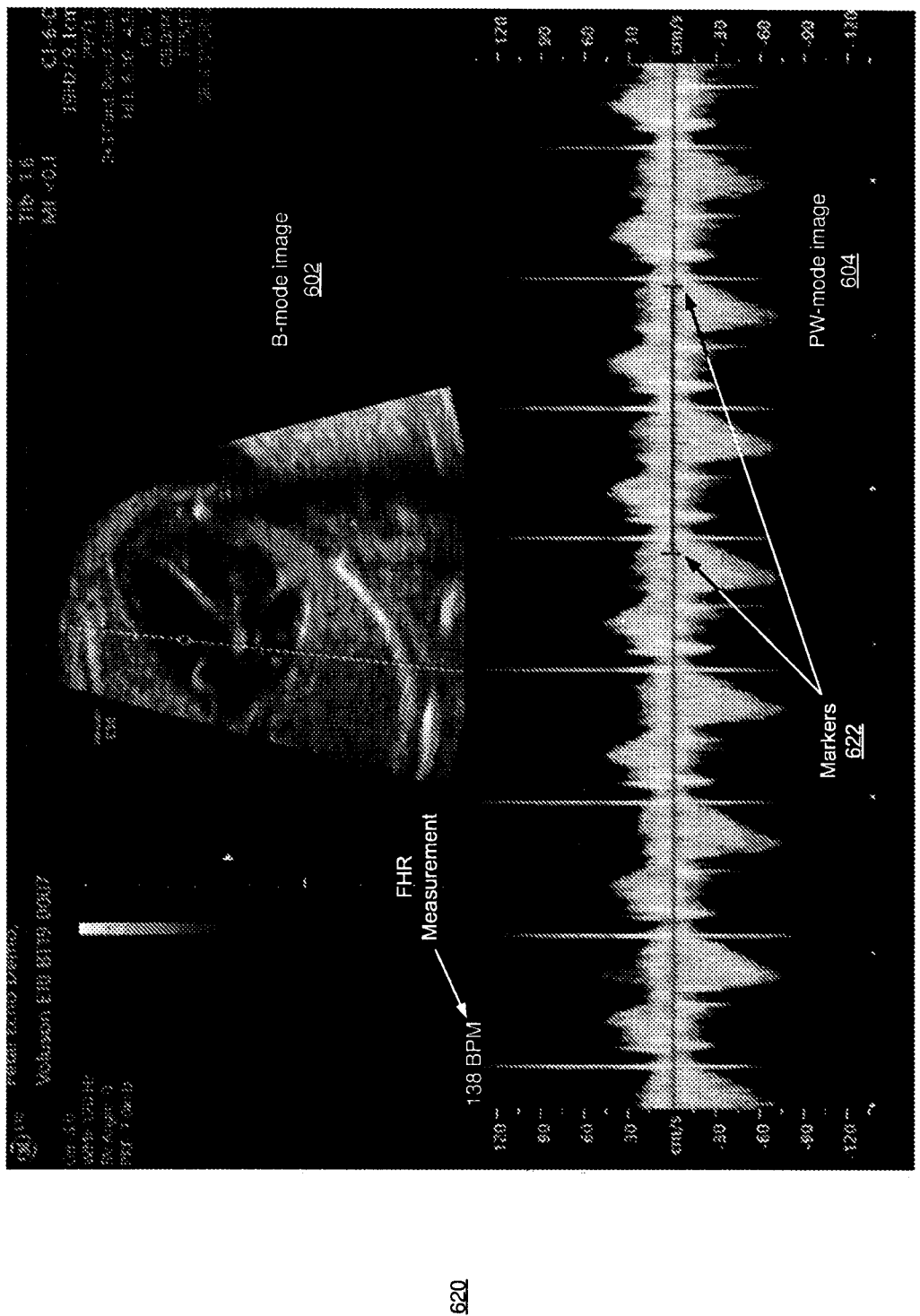

FIG. 6C illustrates screenshot 620, showing placement of calipers/markers during automated heartrate measurement. In particular, two markers (calipers) 622 are determined in the system and placed (displayed) on the PW-mode image 604. The markers 622 (and positions thereof) may be determined automatically in the system, such as based on processing of captured images, specifically the HR and quality scores for particular time sequence, as described with respect to FIG. 6B. In this regard, with reference to the data shown in graph 610, the position of the first (left) marker is set to the position with the highest score based on the data in the graph (e.g., position 540) as shown in screenshot 620.

However, while the correct heartrate may be determined and displayed, in some instances the placement of the markers may not be ideal (as shown in the example screen illustrated in FIG. 6C), as a user may not place the calipers in the manner shown in screenshot 620—that is, at the positions of the markers 622—since there may be no prominent visible structure(s). This may be addressed by further optimizing the placement of the markers. In particular, this may be done by further analysis of the data, to determine positions that may correspond to such structures. For example, the data may analyzed to determine nearby with higher brightness score, which may correspond to such structure.

Figure 6D:
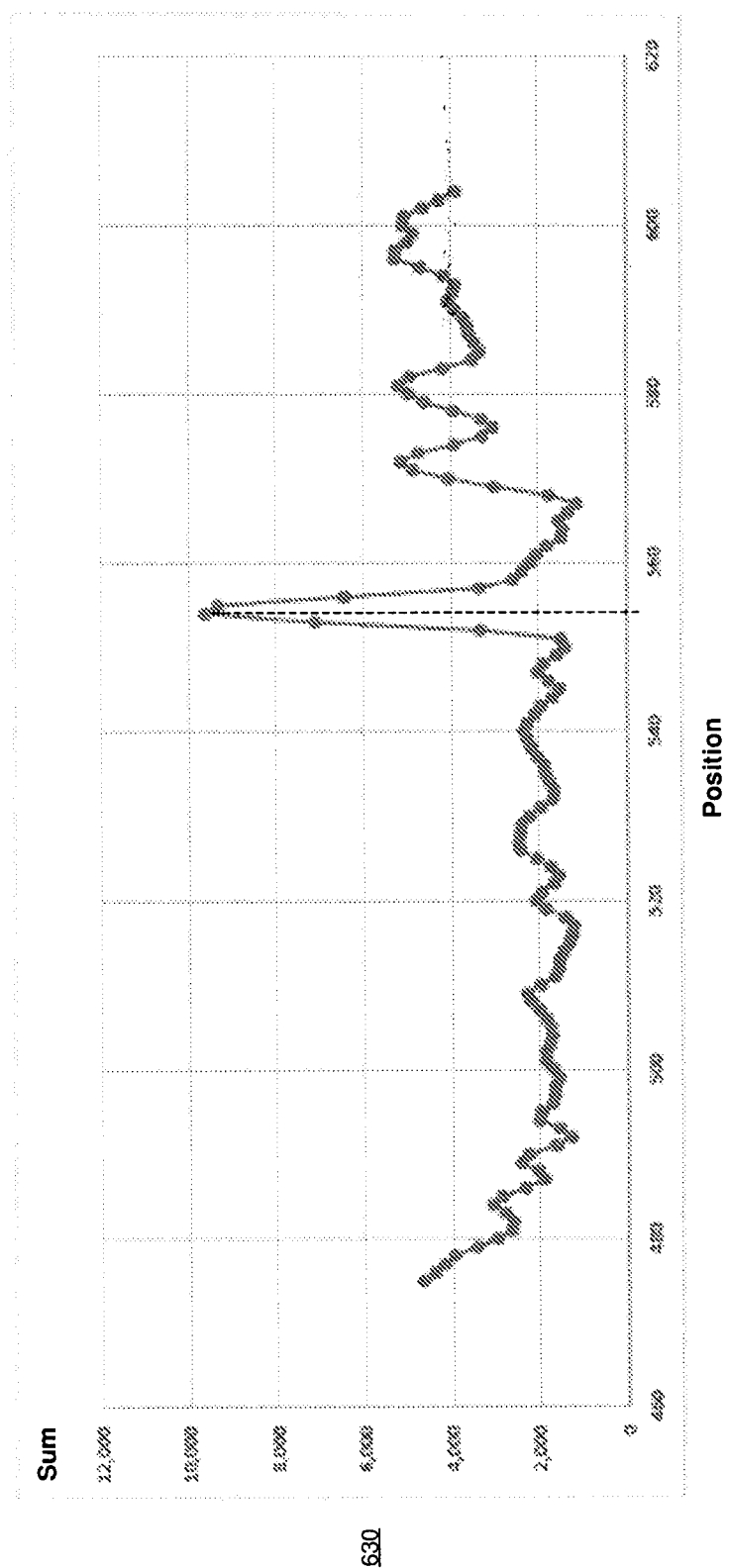

FIG. 6D illustrates a graph 630 sum of lines around the start position determined in a sliding window (e.g., based on HR and quality scores) used for analysis during the automated heart rate measurement. For example, when determining the "brightness" (sum) of lines around the position determined based on graph 610—that is, position 540, it may be determined that the maximum brightness is at position 554. Thus, the start position may be set instead to that position, with the first marker displayed be set at that position.

Figure 6E:
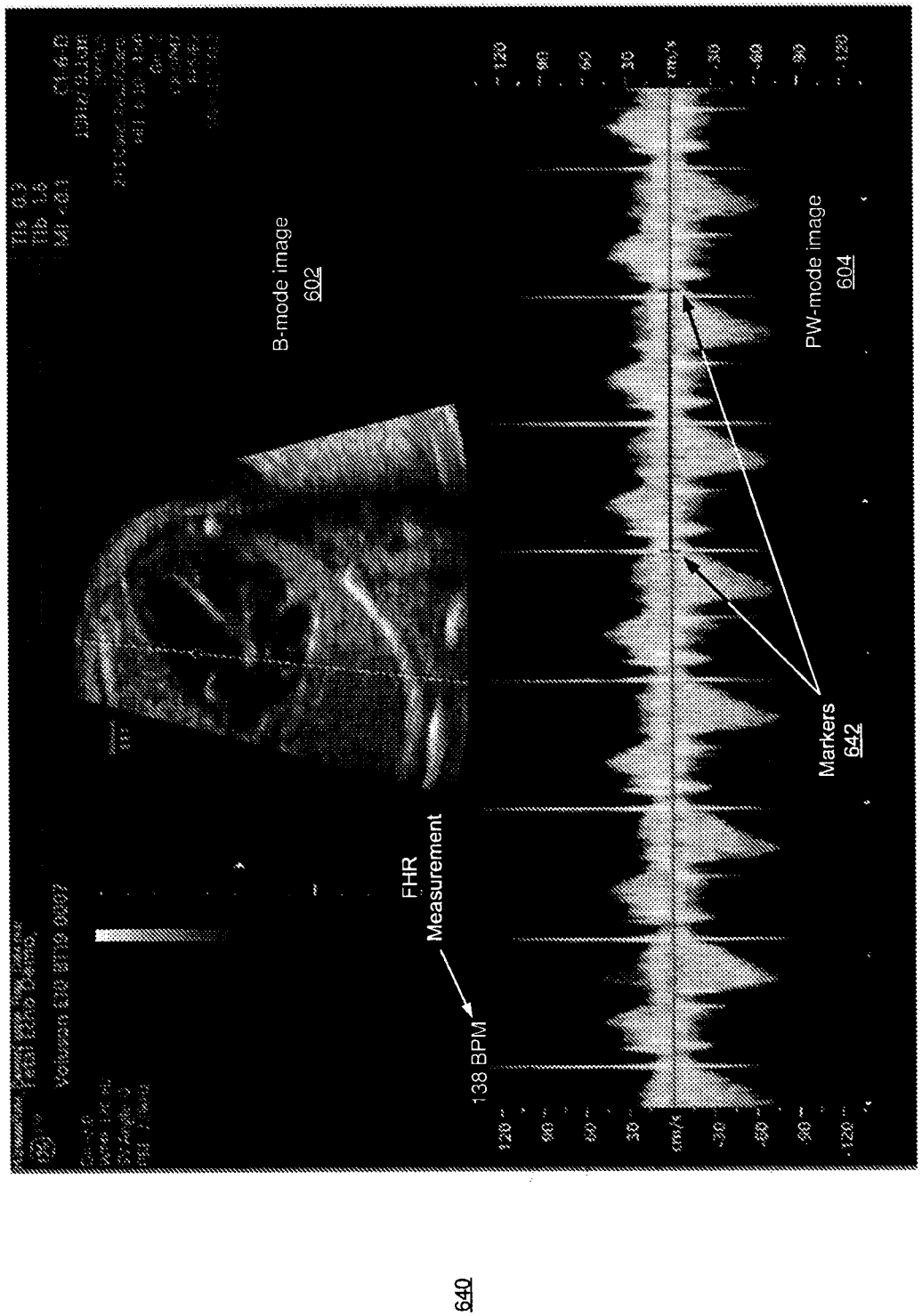

FIG. 6E illustrates screenshot 640, showing use of automated heartrate measurement, with optimized marker placement. In this regard, two markers (calipers) 642 are determined in the system and are placed (displayed) on the PW-mode image, with the position of the first marker being adjusted (optimized) based on the brightness (sum) analysis of area around the initial determined position. The position of the second marker (both before and after optimization) is set and displayed based on the position of the first marker, such as after a number two heart beats (e.g., two heartrates). In this regard, as noted above, the number of heart beats may be configurable (e.g., based on user input or pre-defined parameters).

An example system for automated heart rate measurement, in accordance with the present disclosure, comprises a medical imaging device that comprises at least one processor, with the medical imaging device being configured to, during a medical examination of an area that comprises at least a part of a heart, acquire dataset based on medical imaging technique, generate based on the acquired dataset, one or more medical images, and display the one or more medical images via a display device. The processor is configured to, in real-time, process at least one of the one or more medical images or imaging data corresponding to the at least one of the one or more medical images, automatically determine, based on processing of the at least one of the one or more medical images or the imaging data, position of at least one of a plurality of calipers used in measuring heartrate, and indicate the plurality of calipers in the one or more medical images, based on the position of the at least one of the plurality of calipers, during the displaying of the one or more medical image.

In an example embodiment, the processor is further configured to determine the position of the at least one of the plurality of calipers based on at least one structure of the heart.

In an example embodiment, the processor is further configured to automatically identify the at least one structure of the heart, based on processing of the at least one of the one or more medical images or the imaging data.

In an example embodiment, the processor is further configured to determine a position of at least another one of the plurality of calipers based on the position of the at least one of the plurality of calipers and measured heartrate.

In an example embodiment, the processor is further configured to generate timing-scale based image or dataset, corresponding to the at least one of the one or more medical images, and determine the position of the at least one of the plurality of calipers based on the timing-scale based image or dataset.

In an example embodiment, the processor is further configured to automatically select a sliding window corresponding to a portion of the timing-scale based image or dataset, and determine for each position of the sliding window corresponding parameters relating to one or both of heartrate and quality, with each position corresponding to one of a plurality of samples or lines within at least a portion of the timing-scale based image or dataset.

In an example embodiment, the processor is further configured to assess the parameters corresponding to a plurality of positions of the sliding window, and determine the position of the at least one of the plurality of calipers based on the assessing of the parameters.

In an example embodiment, the processor is further configured to set or adjust the position of the at least one of the plurality of calipers based on pre-defined quality criteria, the quality criteria comprising visual perception by a user of the system.

An example non-transitory computer readable medium, in accordance with the present disclosure, may have stored thereon it a computer program having at least one code section, the at least one code section being executable by a machine comprising at least one processor, for causing the machine to perform one or more steps comprising acquiring dataset based on medical imaging technique, during a medical examination of an area that comprises at least a part of a heart, generating based on the acquired dataset, one or more medical images, displaying the one or more medical images, and during the medical examination, in real-time, processing at least one of the one or more medical images or imaging data corresponding to the at least one of the one or more medical images, automatically determining, based on processing of the at least one of the one or more medical images or the imaging data, position of at least one of a plurality of calipers used in measuring heartrate, and indicating the plurality of calipers in the one or more medical images, based on the position of the at least one of the plurality of calipers, during the displaying of the one or more medical image.

In an example embodiment, the one or more steps further comprise determine the position of the at least one of the plurality of calipers based on at least one structure of the heart.

The non-transitory computer readable medium of claim 10, wherein the one or more steps further comprise automatically identifying the at least one structure of the heart, based on processing of the at least one of the one or more medical images or the imaging data.

In an example embodiment, the one or more steps further comprise determining a position of at least another one of the plurality of calipers based on the position of the at least one of the plurality of calipers and measured heartrate.

In an example embodiment, the one or more steps further comprise generating timing-scale based image or dataset, corresponding to the at least one of the one or more medical images, and determining the position of the at least one of the plurality of calipers based on the timing-scale based image or dataset.

In an example embodiment, the one or more steps further comprise automatically selecting a sliding window corresponding to a portion of the timing-scale based image or dataset, and determining for each position of the sliding window corresponding parameters relating to one or both of heartrate and quality, with each position corresponding to one of a plurality of samples or lines within at least a portion of the timing-scale based image or dataset.

In an example embodiment, the one or more steps further comprise assessing the parameters corresponding to a plurality of positions of the sliding window, and determining the position of the at least one of the plurality of calipers based on the assessing of the parameters.

In an example embodiment, the one or more steps further comprise setting or adjusting the position of the at least one of the plurality of calipers based on pre-defined quality criteria, the quality criteria comprising visual perception by a user of the system.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system comprising:
a medical imaging device comprising at least one processor, wherein the medical imaging device is configured to, during a medical examination of an area that comprises at least a part of a heart:
acquire a dataset based on a medical imaging technique;
generate based on the acquired dataset, one or more medical images; and
display the one or more medical images via a display device; and
wherein the at least one processor is configured to, in real-time:
process at least one of the one or more medical images;
automatically determine, based on processing of the at least one of the one or more medical images, position of at least one of a plurality of calipers used in measuring heartrate;
automatically indicate the plurality of calipers in the one or more medical images, based on the position of the at least one of the plurality of calipers, during the displaying of the one or more medical image;
generate timing-scale based image, corresponding to the at least one of the one or more medical images;
determine the position of the at least one of the plurality of calipers based on the timing-scale based image;
automatically select a sliding window corresponding to a portion of the timing-scale based image;
determine for each position of the sliding window corresponding parameters relating to one or both of heartrate and quality, wherein each position corresponds to one of a plurality of samples or lines within at least a portion of the timing-scale based image;
assess the parameters corresponding to a plurality of positions of the sliding window; and
determine the position of the at least one of the plurality of calipers based on the assessing of the parameters.

2. The system of claim 1, wherein the at least one processor is configured to determine the position of the at least one of the plurality of calipers based on at least one structure of the heart.

3. The system of claim 2, wherein the at least one processor is configured to automatically identify the at least one structure of the heart, based on processing of the at least one of the one or more medical images.

4. The system of claim 1, wherein the at least one processor is configured to determine a position of at least another one of the plurality of calipers based on the position of the at least one of the plurality of calipers and measured heartrate.

5. The system of claim 1, wherein the at least one processor is configured to set or adjust the position of the at least one of the plurality of calipers based on pre-defined quality criteria, the quality criteria comprising visual perception by a user of the system.

6. A non-transitory computer readable medium having stored thereon, a computer program having at least one code section, the at least one code section being executable by a machine comprising at least one processor, for causing the machine to perform one or more steps comprising:
acquiring a dataset based on a medical imaging technique, during a medical examination of an area that comprises at least a part of a heart;
generating based on the acquired dataset, one or more medical images;
displaying the one or more medical images; and
during the medical examination, in real-time:
processing at least one of the one or more medical images;
automatically determining, based on processing of the at least one of the one or more medical images, position of at least one of a plurality of calipers used in measuring heartrate;
automatically indicating the plurality of calipers in the one or more medical images, based on the position of the at least one of the plurality of calipers, during the displaying of the one or more medical image;
generating timing-scale based image, corresponding to the at least one of the one or more medical images;
determining the position of the at least one of the plurality of calipers based on the timing-scale based image;
automatically selecting a sliding window corresponding to a portion of the timing-scale based image;
determining for each position of the sliding window corresponding parameters relating to one or both of heartrate and quality, wherein each position corresponds to one of a plurality of samples or lines within at least a portion of the timing-scale based image;
assessing the parameters corresponding to a plurality of positions of the sliding window; and
determining the position of the at least one of the plurality of calipers based on the assessing of the parameters.

7. The non-transitory computer readable medium of claim 6, wherein the one or more steps further comprise determine the position of the at least one of the plurality of calipers based on at least one structure of the heart.

8. The non-transitory computer readable medium of claim 7, wherein the one or more steps further comprise automatically identifying the at least one structure of the heart, based on processing of the at least one of the one or more medical images.

9. The non-transitory computer readable medium of claim 6, wherein the one or more steps further comprise determining a position of at least another one of the plurality of calipers based on the position of the at least one of the plurality of calipers and measured heartrate.

10. The non-transitory computer readable medium of claim 6, wherein the one or more steps further comprise setting or adjusting the position of the at least one of the plurality of calipers based on pre-defined quality criteria, the quality criteria comprising visual perception by a user of the system.

\* \* \* \* \*